United States Patent
Mamedov et al.

(10) Patent No.: US 7,449,426 B2
(45) Date of Patent: Nov. 11, 2008

(54) CATALYST COMPOSITION WITHOUT ANTIMONY OR MOLYBDENUM FOR AMMOXIDATION OF ALKANES, A PROCESS OF MAKING AND A PROCESS OF USING THEREOF

(75) Inventors: Edouard A. Mamedov, Houston, TX (US); Shahid N. Shaikh, Houston, TX (US); Armando Araujo, Houston, TX (US)

(73) Assignee: Saudi Basic Industries Corporation, Riyadh (SA)

( * ) Notice: Subject to any disclaimer, the term of this patent is extended or adjusted under 35 U.S.C. 154(b) by 431 days.

(21) Appl. No.: 11/288,681

(22) Filed: Nov. 29, 2005

(65) Prior Publication Data

US 2007/0123730 A1    May 31, 2007

(51) Int. Cl.
*B01J 23/20* (2006.01)
*C07C 253/26* (2006.01)

(52) U.S. Cl. ...................................... 502/353; 558/320
(58) Field of Classification Search ................. None
See application file for complete search history.

(56) References Cited

U.S. PATENT DOCUMENTS

| | | | |
|---|---|---|---|
| 4,111,983 A | 9/1978 | Kurtz et al. | |
| 4,289,654 A | 9/1981 | Bertolini et al. | |
| 4,746,641 A | 5/1988 | Guttmann et al. | |
| 4,760,159 A | 7/1988 | Suresh et al. | |
| 4,797,381 A | 1/1989 | Bartek et al. | |
| 4,871,706 A | 10/1989 | Brazdil et al. | |
| 4,873,215 A | 10/1989 | Brazdil et al. | |
| 4,883,895 A | 11/1989 | Brazdil et al. | |
| 4,978,764 A | 12/1990 | Seely et al. | |
| 5,079,207 A | 1/1992 | Brazdil et al. | |
| 5,281,745 A | 1/1994 | Ushikubo et al. | |
| 5,336,804 A | 8/1994 | Blanchard et al. | |
| 5,470,815 A | 11/1995 | Kim et al. | |
| 6,162,760 A | 12/2000 | Brazdil | |
| 6,514,902 B1 | 2/2003 | Inoue et al. | |
| 6,693,059 B2 | 2/2004 | Lin | |
| 7,186,670 B2 * | 3/2007 | Mamedov et al. | 502/353 |

* cited by examiner

*Primary Examiner*—Kamal A Saeed
(74) *Attorney, Agent, or Firm*—Jim Wheelington

(57) ABSTRACT

Disclosed is a catalyst composition which does not contain antimony or molybdenum for the vapor phase ammoxidation of alkanes of the general empirical formula:

$$VW_aBi_bM_cO_x$$

wherein M is one or more elements selected from sodium, cesium, magnesium, calcium, barium, boron, yttrium, indium, aluminum, gallium, tin, titanium, silicon, zirconium, germanium, niobium and tantalum, a is 0.2 to 10, b is 0.5 to 5, c is 0 to 10 and x is determined by the valence requirements of the elements present. The catalyst precursor is precipitated from a solution or slurry of compounds of vanadium, tungsten, bismuth and, optionally, M, then separated, dried and calcined to give a phase or combination of phases active in the ammoxidation of low-weight paraffins to the corresponding unsaturated mononitriles. Nitriles may be produced in a gas phase catalytic reaction of alkanes with ammonia and oxygen in the presence of the catalyst.

53 Claims, No Drawings

CATALYST COMPOSITION WITHOUT ANTIMONY OR MOLYBDENUM FOR AMMOXIDATION OF ALKANES, A PROCESS OF MAKING AND A PROCESS OF USING THEREOF

BACKGROUND OF THE INVENTION

1. Field of the Invention

The invention relates to a catalyst for the catalytic ammoxidation of alkanes, more specifically $C_3$ to $C_5$ paraffins, such as propane or isobutane, to the corresponding $\alpha,\beta$-unsaturated mononitriles, e.g. acrylonitrile and methacrylonitrile. The disclosed catalyst can be utilized also for the ammoxidation of olefins, such as propylene and isobutylene, to the same nitriles. In addition, the catalyst may be used in the ammoxidation of xylenes and methylpyridines to the corresponding mono- and dinitriles.

The invention is directed also to making the catalyst by precipitating, drying and calcining the catalyst precursor to produce active phases with the right proportion. The invention is directed also to using the catalyst in a process for catalytic ammoxidation of alkanes.

2. Description of the Prior Art

Nitriles, such as acrylonitrile and methacrylonitrile, are useful as intermediates for the preparation of fibers, synthetic resins, synthetic rubbers, and the like. One method for producing such nitriles is a gas phase reaction at a high temperature of an olefin, such as propene or isobutene, with ammonia and oxygen in the presence of a catalyst. Known catalysts for conducting this reaction include Mo-based and Sb-based oxides. However, in view of the price difference between propane and propene or between isobutane and isobutene, there are advantages for development of a method for producing acrylonitrile or methacrylonitrile by an ammoxidation reaction with a lower alkane, such as propane or isobutane, as a starting material, which is catalytically reacted with ammonia and oxygen in a gaseous phase in the presence of a catalyst. The majority of effective catalysts reported for propane ammoxidation generally contain vanadium oxides in combination with oxides of antimony and/or molybdenum.

A number of patents assigned to the Standard Oil Company disclose V-Sb oxide catalysts promoted with different elements and various procedures for preparation of those. For instance, U.S. Pat. Nos. 4,746,641 and 4,797,381 disclose paraffin ammoxidation catalysts that contain tungsten in addition to vanadium and antimony. U.S. Pat. Nos. 4,871,706 and 4,873,215 disclose V-Sb oxide catalysts with tungsten and phosphorus. U.S. Pat. No. 5,079,207 discloses a catalyst with tellurium or bismuth in addition to vanadium-antimony. Bismuth is also optionally present in the vanadium-antimony based catalyst claimed in the U.S. Pat. No. 6,162,760. U.S. Pat. No. 5,336,804 discloses vanadium-antimony based catalysts in which bismuth is always present and iron, gallium, indium and mixtures thereof are optionally present.

A molybdenum-based catalyst for propane ammoxidation is the Mo—V—Nb—Te oxide system is disclosed in the U.S. Pat. No. 5,281,745. This catalyst may optionally contain tungsten, bismuth and other elements. U.S. Pat. No. 4,978,764 discloses Bi—Fe—Mo based oxide catalysts in which bismuth must be present and tungsten is optionally present. U.S. Pat. No. 5,470,815 describes In—Ga—Bi—Mo based oxide catalysts that contain always bismuth and optionally tungsten. U.S. Pat. No. 4,760,159 discloses a propane ammoxidation catalyst having the formula $Bi_aV_bL_lM_mT_tO_x$, in which Bi, V, M (selected from among Mo, W, Cr, Ge and Sb) and oxygen are necessarily present. From a number of examples set forth in this patent, it comes that best selectivities to acrylonitrile are obtained on catalysts containing vanadium, bismuth and molybdenum and, optionally, another metal such as chromium, potassium, zinc, cesium or antimony. One example uses a catalyst based on vanadium, bismuth and tungsten of the formula $Bi_1V_{0.7}W_{0.5}O_x$ and deposited onto a silica/alumina mixture in an amount of 50% by weight. This catalyst, however, produces acrylonitrile with the selectivity considerably lower than that attained on catalysts containing molybdenum.

U.S. Pat. Nos. 4,111,983 and 4,289,654 claim an improved process for acrolein oxidation to acrylic acid using Mo—V based oxide catalysts, which necessary contain tungsten. Bismuth is not mentioned even to be an optional element. U.S. Pat. No. 6,693,059 describes a method for preparing catalyst for propane oxidation to acrylic acid having the formula $W_aV_bX_xY_yO_n$, wherein X is at least one element selected from the group consisting of Te, Bi, Sb and Se. The examples listed in this patent use catalysts that contain tellurium along with tungsten and vanadium. None of them contains bismuth. Also, there is no mention of the usefulness of these catalysts for ammoxidation reactions.

U.S. Pat. No. 6,514,902 discloses a process for producing acrylonitrile or methacrylonitrile from propane or isobutane with a catalyst containing at least molybdenum, vanadium and antimony and optionally niobium, tungsten, chromium, titanium, tantalum, zirconium, hafnium, manganese, rhenium, iron, ruthenium, cobalt, rhodium, nickel, palladium, platinum, copper, silver, zinc, boron, gallium, indium, germanium, tin, tellurium, phosphorus, lead, bismuth, rare earth elements and alkaline earth metals wherein the catalyst is made by subjecting a raw material mixtures solution or slurry to an oxidation treatment.

U.S. Pat. No. 4,883,895 discloses a process of catalytic ammoxidation of propane and isobutane to acrylonitrile and methacrylonitrile with a first catalyst composition containing vanadium, phosphorus, tungsten, one or more of iron, cobalt, nickel, chromium, lead, manganese, zinc, selenium, tellurium, gallium, zirconium, indium or arsenic, one or more of an alkali metal or thallium, optionally, one or more of tin, molybdenum, boron, germanium and, optionally, one or more of calcium, strontium, magnesium, and barium, and a second composition containing bismuth, iron, molybdenum, optionally one or more of an alkali metal, samarium or silver, optionally one or more of manganese, chromium, copper, vanadium, zinc, cadmium or lanthanum, optionally one or more of phosphorus, arsenic, antimony, tellurium, tungsten, boron, tin, lead or selenium and optionally, one or more of cobalt, nickel or alkaline earth metal. In the first catalyst composition, molybdenum is present at no more than 2 atoms per atom of vanadium, bismuth is present at no more than 0.2 atoms per atom of vanadium, antimony is present at no more than 0.01 atom per atom of vanadium and the first catalyst composition is essentially uranium free.

All the above patent documents describe selective oxidation catalysts containing vanadium in combination with antimony or/and molybdenum as major constituents. Among numerous complementary elements, tungsten and bismuth are mentioned. The present invention discloses ammoxidation catalysts in which tungsten and bismuth along with vanadium are basic elements. The claimed catalysts do not contain antimony and molybdenum at all because the presence of these elements deteriorates catalyst behavior in the ammoxidation of propane to acrylonitrile.

SUMMARY OF THE INVENTION

The present invention provides mixed metal oxide catalysts containing vanadium, tungsten and bismuth for the ammoxidation of paraffins to unsaturated mononitriles, in particular the ammoxidation of propane and isobutane to acrylonitrile and methacrylonitrile, respectively.

The present invention provides a method for preparing mixed vanadium-tungsten-bismuth oxides having a phase composition catalytically active in propane ammoxidation to acrylonitrile.

The present invention provides an ammoxidation process for making unsaturated mononitriles from lower paraffins, in particular for producing acrylonitrile and methacrylonitrile from propane and isobutane, using mixed metal oxide catalysts based on vanadium, tungsten and bismuth.

Embodiments, aspects, features and advantages of the present invention will become apparent from the study of the accompanying disclosure and appended claims.

According to one aspect of the invention, there is provided a catalyst system comprising the elements in proportions indicated by the following empirical formula:

$$VW_aBi_bM_cO_x$$

where M is at least one element selected from sodium, cesium, magnesium, calcium, barium, boron, yttrium, indium, aluminum, gallium, tin, titanium, silicon, zirconium, germanium, niobium and tantalum;

$$0.2 \leq a \leq 10$$

$$0.5 \leq b \leq 5$$

$$0 \leq c \leq 10 \text{ and}$$

x is determined by the valence requirements of the elements present.

In another aspect of the present invention, there is a method of preparing a catalyst having the following empirical formula:

$$VW_aBi_bM_cO_x$$

where M, a, b, c and x are as defined above. The method comprises precipitating catalyst precursor from a solution or suspension of vanadium, tungsten, bismuth and M compounds as desired to obtain a particular catalyst composition, removing solvent from the precipitate to form a dried catalyst precursor, and calcining the resultant dried precursor at a final temperature in the range of 500 to 900° C. to form the catalyst with a certain phase composition.

The present invention provides also a process for making α,β-unsaturated mononitriles by gas phase reaction of propane or isobutane, oxygen and ammonia in the presence of a catalyst having the elements and proportions indicated by the empirical formula:

$$VW_aBi_bM_cO_x$$

where M, a, b, c and x are as defined above.

The catalyst may also be used in the ammoxidation of propylene and isobutylene to acrylonitrile and methacrylonitrile, and in the ammoxidation of xylenes and methylpyridines to the corresponding mono- and/or dinitriles.

DESCRIPTION OF EMBODIMENTS OF THE INVENTION

The present invention is for a catalyst comprising the elements in proportions indicated by the following empirical formula:

$$VW_aBi_bM_cO_x$$

where M is at least one element selected from sodium, cesium, magnesium, calcium, barium, boron, yttrium, indium, aluminum, gallium, tin, titanium, silicon, zirconium, germanium, niobium and tantalum; $0.2 \leq a \leq 10$; $0.5 \leq b \leq 5$; $0 \leq c \leq 10$ and x is determined by the valence requirements of the elements present. In one embodiment of the invention, M is one element selected from the group consisting of sodium, magnesium, gallium, yttrium, boron, titanium, tin, silicon, zirconium, germanium, aluminum and niobium. In another embodiment of the invention, M are two elements, one selected from aluminum and niobium and one selected from gallium, indium, sodium, tantalum, aluminum and niobium, with the two elements being different. The catalyst composition of the present invention can contain oxides of elements other than those set forth as long as they do not have a material detrimental effect on the catalyst performance. The M elements or any additional elements may become part of the catalyst composition by co-precipitation with vanadium, tungsten and bismuth or by impregnation by any means known in the art, including incipient wetness, before or after calcination of the catalyst precursor to form the catalyst.

In the method of making the present invention, firstly a catalyst precursor is prepared by precipitation from a solution of compounds of vanadium, tungsten, bismuth and, optionally, M with no compounds of antimony or molybdenum present. In this description, "solution" includes not only a solution wherein a solute is completely dissolved but also a solution in a slurry state wherein a part of the solute is present as undissolved.

The vanadium, tungsten, bismuth and M compounds are preferably to be soluble in water. When material is insoluble in water, an acid or alkali may be added to the solution or the solution may be heated to facilitate dissolution. An example of an acid added to the solution to facilitate dissolution is nitric acid. The solution may be heated to a temperature of from 40 to 90° C. to facilitate the dissolution. Generally, a solution can be prepared by dissolving two and more compounds and then adding the remaining compounds, for instance by adding the vanadium compound to the mixed solution of the tungsten, bismuth and optional M compounds. In the alternative, solutions of each of the vanadium, tungsten, bismuth or M compounds can be prepared separately and the separate solutions mixed.

Exemplary vanadium compounds soluble in water include, without limitation, ammonium metavanadate, vanadyl acetylacetonate, vanadyl chloride, vanadium pentafluoride and other vanadium halides. Exemplary tungsten compounds soluble in water include, without limitation, ammonium tungstates and tungstic acids. Exemplary bismuth compounds include, without limitation, bismuth nitrate, bismuth halides and oxyhalides, bismuth sulfate, bismuth acetate and other bismuth organic salts. The compounds containing an element represented by M include, without limitation, nitrate, chloride, carbonate, oxalate, hydroxide and other preferably soluble compounds.

Separate solutions of these compounds may be admixed or the compounds may be commonly dissolved in a solution to precipitate a catalyst precursor to form a suspension. The precipitation can be carried also with addition, for example, of aqueous ammonia or hydrochloric acid during or at the end of mixing of the salts. This procedure may include obtaining and maintaining, if needed, a given pH. The pH may be adjusted to be within a range of 5 to 10, preferably about 8. It is preferable to heat the suspension to a temperature from 30 to 90° C. to drive the precipitation of the precursor to completion.

In the next step, the precipitate is separated from the solvent liquid by any conventional technique known in the art.

Examples for the present invention are filtration and evaporation. To evaporate the solvent, the suspension is heated to a temperature ranging from 30 to 100° C. until a viscous paste is obtained, which is then dried at atmospheric pressure at a temperature ranging from 30 to 200° C., preferably from 100 to 150° C. The dried catalyst precursor is calcined with final temperature ranging from 500 to 900° C., most preferably from 550 to 650° C., in different atmospheres, preferably in air.

The composite oxides of vanadium, tungsten and bismuth thus obtained can comprise different individual and mixed oxide phases. The presence of particular mixed oxides of bismuth and vanadium or of bismuth and tungsten, such as $BiVO_4$ and $Bi_2WO_6$, positively affects catalyst behavior in terms of its selectivity, while individual oxides, such as $V_2O_5$, $WO_3$ and $Bi_2O_3$, affect negatively by making the catalyst less selective. Provided the appropriate ratios of vanadium, tungsten and bismuth are present and provided a preparation procedure which includes precipitating vanadium, tungsten and bismuth into a mixed metal oxide catalyst precursor and drying and calcining the catalyst precursor as described in the present patent application, catalysts in which mixed oxides, e.g., $BiVO_4$ and $Bi_2WO_6$, predominate over individual oxides, e.g., $V_2O_5$, $WO_3$ and $Bi_2O_3$, can be produced. To produce mixed oxides of bismuth and vanadium or of bismuth and tungsten, such as $BiVO_4$ and $Bi_2WO_6$, the molar ratio of bismuth:vanadium:molybdenum from the compounds in solution should be at least 3:1:1. Catalysts containing M elements may comprise, in addition to the above-listed oxides, tricomponent oxide phases. For instance, a niobium-containing catalyst may have the $Bi_3W_1Nb_9O_{30}$ phase which may contribute to enhanced selectivity.

The catalyst can be employed in the powder form or be shaped, for example, as beads, spheres, pellets, extrudes or crushed particles, according to various known techniques. For the examples below, freshly prepared catalysts were ground to fine powder, tabletted at 20 Kpsi, crushed, sieved to 18-30 mesh and loaded to the reactor.

In an ammoxidation process, the reaction is run in the gas phase by contacting a mixture containing paraffin, ammonia and molecular oxygen, and diluent, if any, with the catalyst of the present invention. The catalyst may be in a fixed bed, or a fluidized bed or a moving bed (riser reactor). There may be one or more catalyst used in the ammoxidation process, but preferably one catalyst. The mole ratio of paraffin to ammonia is usually in the range from 0.5 to 10, preferably from 1 to 2.5, and the mole ratio of paraffin to oxygen is usually from 0.1 to 10, preferably from 0.5 to 2. The mole ratio of gaseous diluent, e.g., $N_2$, He, Ar, $CO_2$ and $H_2O$, to paraffin usually ranges from 0 to 20, preferably from 0 to 10. Higher molar ratios can be used but are usually uneconomical.

In the present process, the paraffin as the starting material is not particularly limited, and it may be any lower alkane having from 2 to 8 carbon atoms. However, from the viewpoint of industrial application of the obtainable nitrites, it is preferred to employ propane or isobutane. Low-weight olefins, such as propylene and isobutylene, can also be employed for production of acrylonitrile and methacrylonitrile, respectively. The process according to the invention is more particularly suitable for the ammoxidation of propane.

The reaction temperature can vary from 350 to 550° C., preferably from 425 to 500° C. The latter temperature range is especially useful in the case of propane ammoxidation to acrylonitrile.

The pressure of the reaction can be greater than or equal to atmospheric pressure. It advantageously ranges from 1 to 40 psig. Preferably, pressure is 1 to 20 psig.

The effective contact time is in the range from 0.01 to 10 seconds, but is preferably from 0.05 to 8 seconds, more preferably from 0.1 to 5 seconds.

The most advantageous combination of temperature, pressure and contact time for a given desired result from a given feed can be determined by routine experimentation.

The present invention is described in further detail in the following Examples. However, it should be understood that the present invention is by no means restricted to such specific Examples.

EXAMPLE 1

In a 800 ml beaker, a solution of bismuth nitrate was prepared by dissolving at 40° C. 12.1 g of $Bi(NO_3)_3 \cdot 5H_2O$ in the diluted nitric acid prepared by mixing concentrated acid and de-ionized water in the proportion of 1:8. After 5 minutes of stirring, 0.77 g of solid $(NH_4)_6W_{12}O_{39}$ was added to the bismuth nitrate solution to obtain white slurry. To this slurry, 1.81 g of solid $NH_4VO_3$ was added in small portions at 80° C. and stirred for five minutes to obtain yellow-green slurry. In the next step, water was evaporated by heating the slurry on a hot plate under continuous stirring until the orange-brown paste formed. The paste was transferred to a porcelain dish and dried for 6 hours at 120° C. in the air flow of 250 mL/min. After drying was over, the temperature in the oven was raised to 320° C. at 20° C./min and catalyst precursor was pre-calcined at this temperature for 4 hours. Then the temperature was raised to 520° C. at 20° C./min and the solid was calcined at this final temperature for 6 hours. The product thus prepared had yellow color and nominal composition $VW_{0.2}Bi_{1.6}O_x$. For testing in propane ammoxidation to acrylonitrile, it was ground to fine powder, pressed and sieved to 16-30 mesh.

EXAMPLES 2-7

The catalysts were prepared in the same manner as described in Example 1 except for the following:
1. The amount of ammonium metavanadate was doubled to be 3.62 g.
2. The amounts of ammonium paratungstate and bismuth nitrate are listed in Table 1
3. The resultant compositions were different from Example 1.
4. The physical appearance of the catalyst precursor (paste) and of the finished catalyst and the nominal composition of the catalyst are shown in Table 1.

TABLE 1

| Ex. No | Amount of salt used (g) | | Paste color | Catalyst color | Catalyst composition |
|---|---|---|---|---|---|
| | $(NH_4)_6W_{12}O_{39}$ | $Bi(NO_3)_3 \cdot 5H_2O$ | | | |
| 2 | 3.8 | 24.3 | Orange-brown | Yellow (Y) | $VW_{0.5}Bi_{1.6}O_x$ |
| 3 | 6.1 | 24.3 | Orange | Mustard | $VW_{0.8}Bi_{1.6}O_x$ |
| 4 | 15.3 | 24.3 | Orange | Yellow-green | $VW_{2.0}Bi_{1.6}O_x$ |
| 5 | 6.1 | 7.6 | Orange-brown | Pale-green | $VW_{0.8}Bi_{0.5}O_x$ |

TABLE 1-continued

| Ex. No | Amount of salt used (g) | | Paste color | Catalyst color | Catalyst composition |
|---|---|---|---|---|---|
| | $(NH_4)_6W_{12}O_{39}$ | $Bi(NO_3)_3 \cdot 5H_2O$ | | | |
| 6 | 6.1 | 15.2 | Brown | Yellow-green | $VW_{0.8}Bi_{1.0}O_x$ |
| 7 | 6.1 | 30.4 | Brown | Yellow | $VW_{0.8}Bi_{2.0}O_x$ |

EXAMPLE 8

In a 800 ml beaker, 12.1 g of $Bi(NO_3)_3 \cdot 5H_2O$ was dissolved at 42° C. in 45 ml of the diluted nitric acid prepared by mixing 1 part concentrated acid and 8 parts of de-ionized water. After five minutes of stirring, 3 g of solid $(NH4)_6W_{12}O_{39}$ was added to the above solution at 60° C. to obtain white slurry. To this slurry, a solution of 0.13 g of $NaNO_3$ in 30 ml of de-ionized water was added and stirred to increase the temperature to 75° C. At this temperature, 1.81 g of solid $NH_4VO_3$ was added in small portions and stirred five minutes to obtain light yellow-green slurry. Then the slurry was heated on a hot plate to evaporate the water until orange-brown paste formed. This paste was transferred to a porcelain dish and placed into the oven for drying and calcination in the air flow of 250 mL/min under the following thermal conditions. The temperature in the oven was raised to 120° C. at 20° C./min and held for 6 hours. Then it was increased to 320° C. at 20° C./min and held for 4 hours. And finally, the temperature was ramped up to 600° C. at 20° C./min and held for 6 hours. The catalyst material calcined in this way and cooled to room temperature had yellow color and nominal composition of $VW_{0.8}Bi_{1.6}Na_{0.05}O_x$. For testing in the ammoxidation of propane to acrylonitrile, it was ground to a fine powder, pressed and sieved to 18-30 mesh.

EXAMPLES 9-20

The catalysts in these examples were prepared using the procedure similar to that described in Example 8 including the amounts of ammonium metavanadate, ammonium paratungstate and bismuth nitrate used in preparations. The difference was that instead of sodium nitrate different compounds had been used to prepare catalysts containing other optional M elements in different proportions. The chemical formulae and amounts of utilized M compounds are listed in Table 2 along with the color of catalyst precursor and appearance and composition of finished catalysts.

EXAMPLE 21

Using 800 ml beaker, a solution of bismuth nitrate was prepared by dissolving at room temperature 12.1 g of $Bi(NO_3)_3 \cdot 5H_2O$ in 45 ml of the diluted nitric acid prepared by mixing concentrated acid and de-ionized water in the proportion of 1:8. After stirring this solution for five minutes, 3 g of solid $(NH_4)_6W_{12}O_{39}$ was added to obtain white slurry. To this slurry, 0.78 g of solid $Ga(NO_3)_3$ was added, and the mixture was heated to increase the temperature to 45° C. Once this temperature was attained, 2 g of solid $NbCl_5$ were added in small portions. An exothermic reaction took place that increased the temperature to 62° C. and changed the color of the slurry to light yellow. Then a solution of 1.82 g of $NH_4VO_3$ in 50 ml of de-ionized water was added to this slurry at 95° C. and stirred five minutes to obtain orange precipitate. To separate the precipitate by evaporation of water, the mixture was heated to 95° C. and maintained at this temperature until brown paste formed. The residue was dried at 120° C. for 6 hours, pre-calcined at 320° C. for 4 hours and finally calcined at 600° C. for 6 hours in the air flow of 250 ml/min. The temperature ramp in each step was 20° C./min. Catalyst thus prepared had yellow-grey color and empirical formula $VW_{0.8}Bi_{1.6}Ga_{0.2}Nb_{0.5}O_x$. For testing in propane ammoxidation, it was ground to a fine powder, pressed and sieved to 18-30 mesh.

EXAMPLE 22

In a 800 ml beaker, a solution of bismuth nitrate was prepared by dissolving at 40° C. 12.1 g of $Bi(NO_3)_3 \cdot 5H_2O$ in 45 ml of the diluted nitric acid prepared by mixing one part of concentrated acid and eight parts of de-ionized water. Under stirring, the temperature of solution was raised to 60° C. and 3 g of solid $(NH4)_6W_{12}O_{39}$ was added to obtain white slurry. The temperature of this slurry was increased to 70° C. to add 5.84 g of solid $Al(NO_3)_3 \cdot 9H_2O$ and then to 80° C. to add 2.48 g of solid $In(NO_3)_3 \cdot H_2O$. The resultant mixture was heated to 95° C. and a solution of 1.82 g of $NH_4VO_3$ in 50 ml of de-ionized water was added under stirring to precipitate catalyst precursor of orange color. The water was evaporated by heating the slurry at 95° C. until yellow paste formed. The paste was then transferred to a porcelain dish and dried at

TABLE 2

| Ex. No | M compound | Amount (g) | Paste color | Catalyst color | Catalyst composition |
|---|---|---|---|---|---|
| 9 | $Mg(NO_3)_3 \cdot 5H_2O$ | 0.38 | Light Orange | Yellow | $VW_{0.8}Bi_{1.6}Mg_{0.05}O_x$ |
| 10 | $Ga(NO_3)_3$ | 3.84 | Orange | Yellow | $VW_{0.8}Bi_{1.6}Ga_{0.5}O_x$ |
| 11 | $Y(NO_3)_3 \cdot 6H_2O$ | 2.98 | Orange-brown | Yellow | $VW_{0.8}Bi_{1.6}Y_{0.5}O_x$ |
| 12 | $H_3BO_3$ | 0.10 | Light Orange | Yellow | $VW_{0.8}Bi_{1.6}B_{0.5}O_x$ |
| 13 | $TiCl_4$ | 3.44* | Orange-brown | Beige | $VW_{0.8}Bi_{1.6}Ti_{0.5}O_x$ |
| 14 | $SnCl_4 \cdot 5H_2O$ | 5.26 | Orange-brown | Yellow | $VW_{0.8}Bi_{1.6}Sn_{0.5}O_x$ |
| 15 | $SiCl_4$ | 5.10* | Brown | Yellow | $VW_{0.8}Bi_{1.6}Si_{1.0}O_x$ |
| 16 | $ZrOCl_2 \cdot xH_2O$ | 10.70 | Orange-brown | Yellow | $VW_{0.8}Bi_{1.6}Zr_{2.0}O_x$ |
| 17 | $GeCl_4$ | 1.70* | Red-brown | Yellow | $VW_{0.8}Bi_{1.6}Ge_{0.5}O_x$ |
| 18 | $Al(NO_3)_3 \cdot 9H_2O$ | 5.63 | Beige | Yellow | $VW_{0.8}Bi_{1.6}Al_{1.0}O_x$ |
| 19 | $NbCl_5$ | 4.05 | Light-orange | Yellow | $VW_{0.8}Bi_{1.6}Nb_{0.5}O_x$ |
| 20 | $NbCl_5$ | 12.15 | Orange-brown | Pale-green | $VW_{0.8}Bi_{1.6}Nb_{1.5}O_x$ |

*Added as liquid and not as a solution

120° C. for 6 hours in the air flow of 250 mL/min. Dried precursor was pre-calcined at 320° C. for 4 hours and finally calcined at 600° C. for 6 hours. In both procedures the temperature was increased at 20° C./min. The catalyst thus prepared had yellow color and nominal composition $VW_{0.8}Bi_{1.6}Al_{1.0}In_{0.5}O_x$. For testing in propane ammoxidation reaction, it was ground to a fine powder, pressed and sieved to 18-30 mesh.

EXAMPLES 23-26

The catalysts were prepared in the same manner as described in Example 22 including the used amounts of ammonium metavanadate, ammonium paratungstate, bismuth nitrate and aluminum nitrate which were respectively 1.82, 3.0, 12.1 and 5.84 g. The difference was that instead of indium nitrate the salts of gallium, sodium, niobium or tantalum were utilized to prepare catalysts containing these metals as one more optional M element. Formulae and amounts of used M compounds are listed in Table 3 along with the color of catalyst precursor and appearance and composition of finished catalysts.

TABLE 3

| Ex. No | M compound | Amount (g) | Precursor color | Catalyst color | Catalyst composition |
|---|---|---|---|---|---|
| 23 | $Ga(NO_3)_3$ | 0.77 | Orange-brown | Orange | $VW_{0.8}Bi_{1.6}Al_{1.0}Ga_{0.1}O_x$ |
| 24 | $NaNO_3$ | 0.13 | Light-orange | Yellow | $VW_{0.8}Bi_{1.6}Al_{1.0}Na_{0.05}O_x$ |
| 25 | $NbCl_5$ | 4.05 | Orange-brown | Beige | $VW_{0.8}Bi_{1.6}Al_{1.0}Nb_{0.5}O_x$ |
| 26 | $TaCl_5$ | 10.8 | Mustard | Yellow | $VW_{0.8}Bi_{1.6}Al_{1.0}Ta_{1.0}O_x$ |

Catalysts in Examples 1-26 were tested for propane ammoxidation to acrylonitrile in a ¼ inch I.D. silica-coated stainless steel, fixed bed reactor at atmospheric pressure, 500° C. and flow rate 50 mL/min. The feed consisted of 18% $C_3H_8$, 8% $NH_3$, 15% $O_2$ and balance He. Contact time was varied by changing catalyst amount loaded to the reactor in the range from 1 to 2.5 cc. Catalyst was mixed with quartz chips to have total volume 5 cc. All reactants and reaction products were analyzed on line by gas chromatography. The results of testing catalysts under these conditions assumed to be standard are presented in Table 4.

TABLE 4

| Exam. No. | Catalyst composition | CT[1] (s) | C[2] (%) | Selectivity (%) | | | | |
|---|---|---|---|---|---|---|---|---|
| | | | | $C_3H_6$ | AN[3] | AcN[4] | HCN | $CO_x$ |
| 1 | $VW_{0.2}Bi_{1.6}O_x$ | 2.4 | 1.9 | 6.5 | 2.1 | — | — | 91.4 |
| 2 | $VW_{0.5}Bi_{1.6}O_x$ | 2.4 | 9.3 | 1.9 | 56.0 | — | 5.7 | 37.8 |
| 3 | $VW_{0.8}Bi_{1.6}O_x$ | 2.4 | 10.9 | 1.4 | 55.0 | 0.7 | 8.4 | 34.6 |
| 4 | $VW_2Bi_{1.6}O_x$ | 2.4 | 13.6 | 1.0 | 46.7 | 0.9 | 11.7 | 39.8 |
| 5 | $VW_{0.8}Bi_{0.5}O_x$ | 1.2 | 14.4 | 8.4 | 7.5 | 2.1 | 9.0 | 73.1 |
| 6 | $VW_{0.8}Bi_1O_x$ | 1.8 | 11.5 | 11.3 | 29.8 | 0.9 | 12.6 | 45.4 |
| 7 | $VW_{0.8}Bi_2O_x$ | 3.0 | 8.7 | 1.3 | 39.1 | 1.8 | 1.5 | 56.3 |
| 8 | $VW_{0.8}Bi_{1.6}Na_{0.05}O_x$ | 1.5 | 1.4 | 11.1 | 66.7 | — | 3.2 | 19.0 |
| 9 | $VW_{0.8}Bi_{1.6}Mg_{0.05}O_x$ | 3.0 | 10.0 | 1.8 | 53.7 | — | 8.7 | 35.9 |
| 10 | $VW_{0.8}Bi_{1.6}Ga_{0.5}O_x$ | 1.5 | 13.0 | 10.2 | 56.3 | 2.1 | 8.7 | 22.8 |
| 11 | $VW_{0.8}Bi_{1.6}Y_{0.5}O_x$ | 3.0 | 5.9 | 2.2 | 53.7 | 0.8 | 3.7 | 39.6 |
| 12 | $VW_{0.8}Bi_{1.6}B_{0.5}O_x$ | 3.0 | 7.2 | 1.0 | 55.5 | — | 15.1 | 28.4 |
| 13 | $VW_{0.8}Bi_{1.6}Ti_{0.5}O_x$ | 3.0 | 17.4 | 1.3 | 43.7 | 1.2 | 14.9 | 38.9 |
| 14 | $VW_{0.8}Bi_{1.6}Sn_{0.5}O_x$ | 1.5 | 8.7 | 11.7 | 52.1 | 1.2 | 8.8 | 26.3 |
| 15 | $VW_{0.8}Bi_{1.6}Si_1O_x$ | 1.5 | 7.4 | 16.6 | 51.3 | 2.0 | 12.7 | 17.6 |
| 16 | $VW_{0.8}Bi_{1.6}Zr_2O_x$ | 1.8 | 12.2 | 5.1 | 56.3 | 1.3 | 8.3 | 29.0 |
| 17 | $VW_{0.8}Bi_{1.6}Ge_{0.5}O_x$ | 3.0 | 7.3 | 7.1 | 57.4 | 1.1 | 8.4 | 26.1 |
| 18 | $VW_{0.8}Bi_{1.6}Al_1O_x$ | 1.8 | 10.8 | 4.3 | 65.1 | 1.7 | 8.3 | 20.7 |
| 19 | $VW_{0.8}Bi_{1.6}Nb_{0.5}O_x$ | 0.9 | 10.8 | 4.1 | 63.8 | 1.6 | 12.9 | 17.7 |
| 20 | $VW_{0.8}Bi_{1.6}Nb_{1.5}O_x$ | 2.1 | 9.0 | 5.0 | 64.6 | 1.7 | 12.2 | 16.5 |
| 21 | $VW_{0.8}Bi_{1.6}Nb_{0.5}Ga_{0.2}O_x$ | 1.2 | 10.8 | 9.0 | 60.5 | 2.0 | 12.3 | 16.3 |
| 22 | $VW_{0.8}Bi_{1.6}Al_1In_{0.5}O_x$ | 2.4 | 11.0 | 9.4 | 50.7 | 2.4 | 4.5 | 31.5 |
| 23 | $VW_{0.8}Bi_{1.6}Al_1Ga_{0.1}O_x$ | 1.8 | 11.8 | 9.2 | 54.4 | 1.7 | 11.9 | 22.8 |
| 24 | $VW_{0.8}Bi_{1.6}Al_1Na_{0.05}O_x$ | 2.4 | 10.0 | 10.9 | 55.2 | 0.9 | 7.8 | 25.3 |
| 25 | $VW_{0.8}Bi_{1.6}Al_1Nb_{0.5}O_x$ | 1.2 | 14.5 | 6.0 | 53.3 | 1.9 | 15.4 | 23.5 |
| 26 | $VW_{0.8}Bi_{1.6}Al_1Ta_1O_x$ | 1.2 | 9.5 | 10.1 | 63.8 | 2.3 | 10.6 | 12.9 |

[1]CT is contact time, seconds
[2]C is propane conversion, percent
[3]AN is acrylonitrile
[4]AcN is acetonitrile The catalyst of the present invention does not contain any significant amount of antimony or molybdenum. The essential absence of the antimony and molybdenum is a critical feature of the present invention. The presence of antimony or molybdenum negatively affects catalyst performance especially in the ammoxidation of propane to acrylonitrile.

COMPARATIVE EXAMPLE 1

Five antimony-containing catalysts $VW_{0.8}Bi_{1.6}Sb_yO_x$ where y was 0.25, 0.5, 1, 2, 4, 7 and 10, were prepared by the method described above in Example 8. The only difference was that instead of sodium nitrate we used the antimony trichloride which was added in different amounts to the reference $VW_{0.8}Bi_{1.6}O_x$ catalyst.

In a 800 ml beaker, a solution of bismuth nitrate was prepared by dissolving at 40° C. 12.1 g of $Bi(NO_3)_3.5H_2O$ in the 38 ml of diluted nitric acid prepared by mixing concentrated acid and de-ionized water in the proportion of 1:8. After 5 minutes of stirring, a solution of 3 g of $(NH4)6W_{12}O_{39}$ in 30 ml of de-ionized water was added at 60° C. to the bismuth nitrate solution to obtain white slurry. To this slurry, solid $SbCl_3.xH_2O$ was added to in small portions via spatula at ~70° C. (the amount of added antimony trichloride varied from 1.7 to 68 g to prepare catalysts with different content of antimony). An exothermic reaction occurred and brown fumes of $NO_2$ were given off. After 10 minutes of reaction, the color of slurry became white. To this slurry, 1.81 g of solid $NH_4VO_3$ was added in small portions at 80° C. and stirred for 10 minutes to obtain yellow-green slurry which in 15 minutes changed color to red-brown. In the next step, water was evaporated by heating the slurry on a hot plate under continuous stirring until an orange-brown paste was formed. The paste was transferred to a porcelain dish and dried for 6 hours at 120° C. in an air flow of 250 ml/min. After drying was over, the temperature in the oven was raised to 320° C. at 20° C./min and catalyst precursor was pre-calcined at this temperature for 4 hours. Then the temperature was raised to 600° C. at 20° C./min and the solid was calcined at this final temperature for 6 hours. After calcinations, yellow-green material was obtained (high antimony catalysts had beige-gray color). For testing in propane ammoxidation to acrylonitrile, it was ground to fine powder, pressed and sieved to 18-30 mesh.

COMPARATIVE EXAMPLE 2

Three molybdenum-containing catalysts $VW_{0.8}Bi_{1.6}Mo_yO_x$, where y was 0.5, 1 and 2, were prepared by the method described above in Example 8. The only difference was that instead of sodium nitrate we used the ammonium heptamolybdate which was added in different amounts to the reference $VW_{0.8}Bi_{1.6}O_x$ catalyst.

In a 800 ml beaker, a solution of bismuth nitrate was prepared by dissolving at 40° C. 12.1 g of $Bi(NO_3)_3.5H_2O$ in the 38 ml of diluted nitric acid prepared by mixing concentrated acid and de-ionized water in the proportion of 1:8. After 5 minutes of stirring, a solution of 3 g of $(NH_4)_6W_{12}O_{39}$ in 30 ml of de-ionized water was added at 60° C. to the bismuth nitrate solution to obtain white slurry. To this slurry, solid $(NH_4)_6Mo_7O_{24}$ was added in small portions via spatula at ~60° C. (the amounts of ammonium heptamolybdate added were 1.4, 2.8 and 5.6 g to prepare catalysts with different content of molybdenum). An exothermic reaction occurred and brown fumes of $NO_2$ were given off. After 10 minutes of reaction, the color of slurry became white. To this slurry, 1.81 g of solid $NH_4VO_3$ was added in small portions at 80° C. and stirred for 10 minutes to obtain yellow-green slurry which in 20 minutes changed color to orange. In the next step, water was evaporated by heating the slurry on a hot plate under continuous stirring until an orange paste formed. The paste was transferred to a porcelain dish and dried for 6 hours at 120° C. in an air flow of 250 ml/min. After drying was over, the temperature in the oven was raised to 320° C. at 20° C./min and catalyst precursor was pre-calcined at this temperature for 4 hours. Then the temperature was raised to 600° C. at 20° C./min and the solid was calcined at this final temperature for 6 hours. After calcinations, yellow-gray material was obtained. For testing in propane ammoxidation to acrylonitrile, it was ground to fine powder, pressed and sieved to 18-30 mesh.

Catalysts in the Comparative Examples were tested for propane ammoxidation to acrylonitrile in a ¼ inch I.D. silica-coated stainless steel, fixed bed reactor at atmospheric pressure, 500° C. and flow rate 50 mL/min. The feed consisted of 18% $C_3H_8$, 8% $NH_3$, 15% $O_2$ and balance He. Contact time was varied by changing catalyst amount loaded to the reactor in the range from 0.5 to 2.5 cc. Catalyst was mixed with quartz chips to have total volume 5 cc. All reactants and reaction products were analyzed on line by gas chromatography.

As the amount of antimony increases over a Sb:V molar ratio of 4:1, the propane conversion decreases. As the amount of antimony increases over a Sb:V molar ratio of 0:1, the acrylonitrile selectivity decreases. As the amount of molybdenum increases over a Mo:V molar ratio of 0:1, the propane conversion decreases. As the amount of molybdenum increases over a Mo:V molar ratio of 0:1, the acrylonitrile selectivity decreases.

As noted above, the presence of particular mixed oxides of bismuth and vanadium or of bismuth and tungsten, such as $BiVO_4$ and $Bi_2WO_6$, positively affects catalyst behavior in terms of its selectivity, while individual oxides, such as $V_2O_5$, $WO_3$ and $Bi_2O_3$, have a negative effect by making the catalyst less selective.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letter of Patent of the United States of America is:

1. A catalyst composition for vapor phase ammoxidation of alkanes and olefins comprising a compound of the formula:

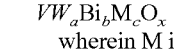

$VW_aBi_bM_cO_x$ wherein M is one or more elements selected from sodium, cesium, magnesium, calcium, barium, boron, yttrium, indium, aluminum, gallium, tin, titanium, silicon, zirconium, germanium, niobium and tantalum, a is 0.2 to 10, b is 0.5 to 5, c is 0 to 10 and x is determined by the valence requirements of the elements present and wherein antimony and molybdenum are not present.

2. The catalyst composition of claim 1 wherein M is one element selected from the group consisting of sodium, magnesium, gallium, yttrium, boron, titanium, tin, silicon, zirconium, germanium, aluminum and niobium.

3. The catalyst composition of claim 1 wherein M are two elements, one selected from the group consisting of aluminum and niobium and one selected from the group consisting of gallium, indium, sodium, tantalum, aluminum and niobium, with the two elements being different.

4. The catalyst composition of claim 1 wherein one or more mixed oxide selected from the group consisting of $BiVO_4$ and $Bi_2WO_6$ is present.

5. The catalyst composition of claim 1 wherein the mixed oxide $Bi_3W_1Nb_9O_{30}$ is present.

6. The catalyst composition of claim 1 wherein the compound is $VW_{0.2}Bi_{1.6}O_x$, $VW_{0.5}Bi_{1.6}O_x$, $VW_{0.8}Bi_{1.6}O_x$, $VW_2Bi_{1.6}O_x$, $VW_{0.8}Bi_{0.5}O_x$, $VW_{0.8}Bi_1O_x$, $VW_{0.8}Bi_2O_x$, $VW_{0.8}Bi_{1.6}Na_{0.05}O_x$, $VW_{0.8}Bi_{1.6}Mg_{0.05}O_x$, $VW_{0.8}Bi_{1.6}Ga_{0.5}O_x$, $VW_{0.8}Bi_{1.6}Y_{0.5}O_x$, $VW_{0.8}Bi_{1.6}B_{0.5}O_x$, $VW_{0.8}Bi_{1.6}Ti_{0.5}O_x$, $VW_{0.8}Bi_{1.6}Sn_{0.5}O_x$, $VW_{0.8}Bi_{1.6}Si_1O_x$, $VW_{0.8}Bi_{1.6}Zr_2O_x$, $VW_{0.8}Bi_{1.6}Ge_{0.5}O_x$, $VW_{0.8}Bi_{1.6}Al_1O_x$, $VW_{0.8}Bi_{1.6}Nb_{0.5}O_x$, $VW_{0.8}Bi_{1.6}Nb_{1.5}O_x$, $VW_{0.8}Bi_{1.6}Nb_{0.5}Ga_{0.2}O_x$, $VW_{0.8}Bi_{1.6}Al_1In_{0.5}O_x$, $VW_{0.8}Bi_{1.6}Al_1Ga_{0.1}O_x$, $VW_{0.8}Bi_{1.6}Al_1Na_{0.05}O_x$, $VW_{0.8}Bi_{1.6}Al_1Nb_{0.5}O_x$ or $VW_{0.8}Bi_{1.6}Al_1Ta_1O_x$.

7. A process of making a catalyst composition for vapor phase ammoxidation of alkanes and olefins comprising:
 a) forming a solution of a vanadium compound, a tungsten compound, a bismuth compound and, optionally, one or more compounds of M wherein M is selected from the group consisting of sodium, cesium, magnesium, calcium, barium, boron, yttrium, indium, aluminum, gallium, tin, titanium, silicon, zirconium, germanium, niobium and tantalum
 wherein the solution does not contain an antimony compound or a molybdenum compound;
 b) precipitating a catalyst precursor to form a suspension;
 c) separating the catalyst precursor from the suspension;
 d) drying the catalyst precursor; and
 e) calcining the catalyst precursor to form a catalyst of the formula:

$$VW_aBi_bM_cO_x$$

wherein M is one or more elements selected from sodium, cesium, magnesium, calcium, barium, boron, yttrium, indium, aluminum, gallium, tin, titanium, silicon, zirconium, germanium, niobium and tantalum, a is 0.2 to 10, b is 0.5 to 5, c is 0 to 10 and x is determined by the valence requirements of the elements present,
and wherein the catalyst does not contain antimony or molybdenum.

8. The process of claim 7 wherein the solution is formed by:
 a) preparing a separate solution of the vanadium compound, a separate solution of the tungsten compound, a separate solution of the a bismuth compound and, optionally a separate solution of one or more compounds of M; and
 b) mixing the separate solutions together.

9. The process of claim 7 wherein the vanadium compound, the tungsten compound, the bismuth compound and, optionally, one or more compounds of M are commonly dissolved in solution.

10. The process of claim 7 wherein the vanadium compound, the tungsten compound, the bismuth compound and, optionally, one or more compounds of M are dissolved in water to form the solution.

11. The process of claim 7 further comprising adding an acid or an alkali to the solution to form the solution.

12. The process of claim 7 further comprising heating to a temperature of from 30 to 90° C. to form the solution.

13. The process of claim 7 wherein the vanadium compound is ammonium metavanadate, vanadyl acetylacetonate, vanadyl chloride or vanadium pentafluoride.

14. The process of claim 7 wherein the tungsten compound is ammonium tungstate or tungstic acid.

15. The process of claim 7 wherein the bismuth compound is bismuth nitrate, a bismuth halide, a bismuth oxyhalide, bismuth sulfate or bismuth acetate.

16. The process of claim 7 wherein the compound of M is a nitrate, chloride, carbonate, oxalate or hydroxide.

17. The process of claim 7 additionally comprising obtaining and maintaining a pH of the solution in a range from 5 to 10.

18. The process of claim 17 wherein the pH is 8.

19. The process of claim 7 further comprising heating to a temperature in the range from 30° C. to 90° C. to precipitate the catalyst precursor to form a suspension.

20. The process of claim 7 wherein the catalyst precursor is separated from the suspension by filtration or evaporation.

21. The process of claim 20 wherein the catalyst precursor is separated from the suspension by evaporation by heating the suspension to a temperature in the range from 30° C. to 200° C.

22. The process of claim 21 wherein a viscous paste is formed after evaporation.

23. The process of claim 22 wherein the paste is dried at a temperature in the range from 30° C. to 200° C.

24. The process of claim 23 wherein the paste is dried at a temperature in the range from 100° C. to 150° C. and at one atmosphere pressure.

25. The process of claim 7 wherein the catalyst precursor is calcined at a temperature from 500 to 900° C.

26. The process of claim 25 wherein the catalyst precursor is calcined at a temperature from 550 to 650° C.

27. The process of claim 7 wherein the hydroxides are calcined in air.

28. The process of claim 7 wherein the catalyst composition is $VW_{0.2}Bi_{1.6}O_x$, $VW_{0.5}Bi_{1.6}O_x$, $VW_{0.8}Bi_{1.6}O_x$, $VW_2Bi_{1.6}O_x$, $VW_{0.8}Bi_{0.5}O_x$, $VW_{0.8}Bi_1O_x$, $VW_{0.8}Bi_2O_x$, $VW_{0.8}Bi_{1.6}Na_{0.05}O_x$, $VW_{0.8}Bi_{1.6}Mg_{0.05}O_x$, $VW_{0.8}Bi_{1.6}Ga_{0.5}O_x$, $VW_{0.8}Bi_{1.6}Y_{0.5}O_x$, $VW_{0.8}Bi_{1.6}B_{0.5}O_x$, $VW_{0.8}Bi_{1.6}Ti_{0.5}O_x$, $VW_{0.8}Bi_{1.6}Sn_{0.5}O_x$, $VW_{0.8}Bi_{1.6}Si_1O_x$, $VW_{0.8}Bi_{1.6}Zr_2O_x$, $VW_{0.8}Bi_{1.6}Ge_{0.5}O_x$, $VW_{0.8}Bi_{1.6}Al_1O_x$, $VW_{0.8}Bi_{1.6}Nb_{0.5}O_x$, $VW_{0.8}Bi_{1.6}Nb_{1.5}O_x$, $VW_{0.8}Bi_{1.6}Nb_{0.5}Ga_{0.2}O_x$, $VW_{0.8}Bi_{1.6}Al_1In_{0.5}O_x$, $VW_{0.8}Bi_{1.6}Al_1Ga_{0.1}O_x$, $VW_{0.8}Bi_{1.6}Al_1Na_{0.05}O_x$, $VW_{0.8}Bi_{1.6}Al_1Nb_{0.5}O_x$ or $VW_{0.8}Bi_{1.6}Al_1Ta_1O_x$.

29. The process of claim 7 wherein the molar ratio of bismuth:vanadium:molybdenum in the solution it at least 3:1:1.

30. A process for ammoxidation of alkanes and olefins comprising:
 contacting a mixture of an alkane or olefin, ammonia and molecular oxygen in the gas phase with a catalyst composition of the formula:

$$VW_aBi_bM_cO_x$$

wherein M is one or more elements selected from sodium, cesium, magnesium, calcium, barium, boron, yttrium, indium, aluminum, gallium, tin, titanium, silicon, zirconium, germanium, niobium and tantalum, a is 0.2 to 10, b is 0.5 to 5, c is 0 to 10 and x is determined by the valence requirements of the elements present and
wherein antimony and molybdenum are not present.

31. The process of claim 30 herein the catalyst is in a fixed bed, fluidized bed or a moving bed.

32. The process of claim 30 wherein the mole ratio of alkane to ammonia is in the range from 0.5 to 10.

33. The process of claim 30 wherein the mole ratio of alkane to ammonia is in the range from 1 to 2.5.

34. The process of claim 30 wherein the mole ratio of alkane to oxygen is in the range from 0.1 to 10.

35. The process of claim 34 wherein the mole ratio of alkane to oxygen is in the range from 0.5 to 2.

36. The process of claim 30 additionally comprising a diluent in the gas phase selected from the group consisting of nitrogen, helium, argon, carbon dioxide and water.

37. The process of claim 36 wherein the mole ratio of alkane to diluent is in the range from 0 to 20.

38. The process of claim 37 wherein the mole ratio of alkane to diluent is in the range from 0 to 10.

39. The process of claim 30 wherein the alkane has from two to eight carbon atoms.

40. The process of claim 39 wherein the alkane is propane or isobutane.

41. The process of claim 30 wherein contacting the mixture of the alkane or olefin, ammonia and molecular oxygen in the gas phase with the catalyst occurs at a temperature in the range from 350 to 550° C.

42. The process of claim 41 wherein the temperature is in the range from 425 to 500° C.

43. The process of claim 30 wherein contacting the mixture of the alkane or olefin, ammonia and molecular oxygen in the gas phase with the catalyst occurs at a pressure in the range from 1 to 40 psig.

44. The process of claim 43 wherein the pressure is in the range from 1 to 20 psig.

45. The process of claim 44 wherein the pressure is atmospheric.

46. The process of claim 30 wherein contacting the mixture of the alkane or olefin, ammonia and molecular oxygen in the gas phase with the catalyst is at a time in the range from 0.01 to 10 seconds.

47. The process of claim 46 wherein the contact time is from 0.05 to 8 seconds.

48. The process of claim 47 wherein the contact time is from 0.1 to 5 seconds.

49. The process of claim 30 wherein M is one element selected from the group consisting of sodium, magnesium, gallium, yttrium, boron, titanium, tin, silicon, zirconium, germanium, aluminum and niobium.

50. The process of claim 30 wherein M are two elements, one selected from the group consisting of aluminum and niobium and one selected from the group consisting of gallium, indium, sodium, tantalum, aluminum and niobium, with the two elements being different.

51. The process of claim 30 wherein one or more mixed oxide selected from the group consisting of $BiVO_4$ and $Bi_2WO_6$ is present in the catalyst composition.

52. The process of claim 30 wherein the mixed oxide $Bi_3W_1Nb_9O_{30}$ is present in the catalyst composition.

53. The process of claim 30 wherein the catalyst composition is $VW_{0.2}Bi_{1.6}O_x$, $VW_{0.5}Bi_{1.6}O_x$, $VW_{0.8}Bi_{1.6}O_x$, $VW_2Bi_{1.6}O_x$, $VW_{0.8}Bi_{0.5}O_x$, $VW_{0.8}Bi_1O_x$, $VW_{0.8}Bi_2O_x$, $VW_{0.8}Bi_{1.6}Na_{0.05}O_x$, $VW_{0.8}Bi_{1.6}Mg_{0.05}O_x$, $VW_{0.8}Bi_{1.6}Ga_{0.5}O_x$, $VW_{0.8}Bi_{1.6}Y_{0.5}O_x$, $VW_{0.8}Bi_{1.6}B_{0.5}O_x$, $VW_{0.8}Bi_{1.6}Ti_{0.5}O_x$, $VW_{0.8}Bi_{1.6}Sn_{0.5}O_x$, $VW_{0.8}Bi_{1.6}Si_1O_x$, $VW_{0.8}Bi_{1.6}Zr_2O_x$, $VW_{0.8}Bi_{1.6}Ge_{0.5}O_x$, $VW_{0.8}Bi_{1.6}Al_1O_x$, $VW_{0.8}Bi_{1.6}Nb_{0.5}O_x$, $VW_{0.8}Bi_{1.6}Nb_{1.5}O_x$, $VW_{0.8}Bi_{1.6}Nb_{0.5}Ga_{0.2}O_x$, $VW_{0.8}Bi_{1.6}Al_1In_{0.5}O_x$, $VW_{0.8}Bi_{1.6}Al_1Ga_{0.1}O_x$, $VW_{0.8}Bi_{1.6}Al_1Na_{0.05}O_x$, $VW_{0.8}Bi_{1.6}Al_1Nb_{0.5}O_x$ or $VW_{0.8}Bi_{1.6}Al_1Ta_1O_x$.

* * * * *